United States Patent
Babic et al.

(10) Patent No.: US 10,542,959 B2
(45) Date of Patent: Jan. 28, 2020

(54) OBJECT TRACKING DEVICE

(71) Applicant: KONINKLIJKE PHILIPS N.V., Eindhoven (NL)

(72) Inventors: Drazenko Babic, Eindhoven (NL); Robert Johannes Frederik Homan, Eindhoven (NL); Bernardus Hendrikus Wilhelmus Hendriks, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/915,047

(22) PCT Filed: Dec. 5, 2014

(86) PCT No.: PCT/EP2014/076662
§ 371 (c)(1),
(2) Date: Feb. 26, 2016

(87) PCT Pub. No.: WO2015/091015
PCT Pub. Date: Jun. 25, 2015

(65) Prior Publication Data
US 2016/0278731 A1   Sep. 29, 2016

(30) Foreign Application Priority Data
Dec. 19, 2013  (EP) .................................. 13198609

(51) Int. Cl.
*A61B 6/00*  (2006.01)
*A61B 90/00*  (2016.01)
*A61B 6/04*  (2006.01)

(52) U.S. Cl.
CPC ............ *A61B 6/547* (2013.01); *A61B 6/0407* (2013.01); *A61B 6/4417* (2013.01);
(Continued)

(58) Field of Classification Search
CPC .... A61B 2034/2055; A61B 2034/2065; A61B 2090/363; A61B 2090/364;
(Continued)

(56) References Cited

U.S. PATENT DOCUMENTS 6,205,347 B1 * 3/2001 Morgan ................... A61B 6/04
600/407
6,527,443 B1    4/2003 Vilsmeier
(Continued)

FOREIGN PATENT DOCUMENTS

DE    102008050572 A1   4/2010
JP       2012192268 A   10/2012
(Continued)

OTHER PUBLICATIONS

Spetzger, U. et al "Navigational Microneurosurgery: Experience with the EasyGuide Neuro", MEDICAMUNDI, vol. 41, Issue 1, Mar. 1997.

*Primary Examiner* — Ruth S Smith

(57) ABSTRACT

An object tracking device for a medical imaging system tracks a predetermined movable object such as a medical instrument and/or a patient. The object tracking device includes primary and secondary imagers. The primary imager is configured to provide first image data of a patient's body including the interior of a patient's body. The primary imager is movable between imaging and parking modes. The secondary imager is configured to provide second image data of a patient's body including the exterior of a patient's body. The object tracking device further includes a position monitoring arrangement configured to monitor a position of the secondary imager relative to the position of a reference point. As a result, the medical instrument and/or the patient is traceable in the imaging mode based on the image data of
(Continued)

the primary imager, and in the parking mode based on the image data of the secondary imager.

19 Claims, 2 Drawing Sheets

(52) U.S. Cl.
CPC ............ *A61B 6/4441* (2013.01); *A61B 6/461* (2013.01); *A61B 6/54* (2013.01); *A61B 90/39* (2016.02); *A61B 2090/397* (2016.02)

(58) Field of Classification Search
CPC ...... A61B 2090/371; A61B 2090/3764; A61B 2090/3937; A61B 2090/397; A61B 5/002; A61B 5/0035; A61B 5/0077; A61B 5/1113; A61B 6/0407; A61B 6/4417; A61B 6/4441; A61B 6/461; A61B 6/54; A61B 6/547; A61B 90/39
See application file for complete search history.

(56) References Cited

U.S. PATENT DOCUMENTS

| | | |
|---|---|---|
| 2002/0018588 A1 | 2/2002 | Kusch |
| 2006/0079752 A1 | 4/2006 | Auderl |
| 2008/0199059 A1* | 8/2008 | Eck ........................ A61B 6/032 382/128 |
| 2009/0195249 A1* | 8/2009 | DeMeester ............ G01R 33/28 324/318 |
| 2012/0294498 A1 | 11/2012 | Popovic |
| 2013/0218024 A1* | 8/2013 | Boctor .................. A61B 34/20 600/476 |

FOREIGN PATENT DOCUMENTS

| | | |
|---|---|---|
| WO | 2007115825 A1 | 10/2007 |
| WO | 2012149548 A2 | 11/2012 |
| WO | 2013102827 A1 | 7/2013 |

\* cited by examiner

- 102 provide image data by a primary imaging unit
- 104 provide image data by a secondary imaging unit
- 106 determine position of the secondary imaging unit
- 108 track movable object

100

OBJECT TRACKING DEVICE

CROSS-REFERENCE TO PRIOR APPLICATIONS

This application is the U.S. National Phase application under 35 U.S.C. § 371 of International Application No. PCT/EP2014/076662, filed on Dec. 5, 2014, which claims the benefit of European Patent Application No. 13198609.3, filed on Dec. 19, 2013. These applications are hereby incorporated by reference herein.

FIELD OF THE INVENTION

The present invention relates to an object tracking device for a medical imaging system, a medical imaging system, an object tracking method for a medical imaging system, a computer program element for controlling such device and a computer readable medium having stored such computer program element.

BACKGROUND OF THE INVENTION

In image guided minimally invasive therapy, continuous image based guidance may be used while performing patient treatment in a minimally invasive way. A known concept for continuous image based guidance may relate to a rotatable C-shaped arm-based system, which merges continuously a video imaging with an X-ray imaging.

WO 2013/102827 describes a position determining apparatus for determining the position of an interventional instrument within a patient. A spatial relation between positions of a second part of the interventional instrument outside the patient and a first part of the interventional instrument within the patient is determined based on an actual image of the interventional instrument within the patient being preferentially an X-ray image and a provided position of the second part. Once the spatial relation has been determined, the position of the interventional instrument within the patient can be determined, while the interventional instrument is moved within the patient, based on the determined spatial relation and a determined actual position of the second part outside the subject, without necessarily acquiring a further actual image.

Such concept persistently requires having the X-ray detector with the embedded video camera continuously located in its C-shaped arm above, around and below the anatomy of interest in order to track continuously patient and instrument motion. However, the C-shaped arm with the embedded video camera may hinder during the therapy execution due to its large-sized and its position above, around and below the patient.

SUMMARY OF THE INVENTION

Hence, there may be need to provide object tracking, which hinders less during the therapy execution.

The object of the present invention is solved by the subject-matters of the independent claims, wherein further embodiments are incorporated in the dependent claims. It should be noted that the following described aspects of the invention apply also for the object tracking device, for the medical imaging system, for the object tracking method, for the computer program element, and for the computer readable medium.

According to the present invention, a medical imaging system arranged to track a predetermined movable object is presented. The predetermined movable object may be a medical instrument and/or a patient. The object tracking device comprises a primary imaging unit and a secondary imaging unit. The primary imaging unit is configured to provide first image data of a patient's body. It might further be configured to provide image data of the interior of a patient's body. The primary imaging unit is movable between an imaging mode and a parking mode. The imaging mode might be close to a patient's body, while the parking mode might be more remote from a patient's body.

The secondary imaging unit is configured to provide second image data of a patient's body. It might further be configured to provide optical image data of the exterior of a patient's body, e.g. body shape, vital signs, movements, tissue perfusion, skin properties etc. However, the secondary imaging unit might also be exclusively or additionally configured to provide image data of the interior of a patient's body.

The system, in particular the primary imaging unit, is further arranged to determine a position of the secondary imaging unit relative to the position of a reference point. The reference point is preferably the position of the primary imaging unit. However, the reference point might also be a point in the operating room, which position relative to the position of the primary imaging unit is known and which can therefore be used to calculate the position of the secondary imaging unit relative to the position of the primary imaging unit.

Then, a predetermined movable object, e.g. the medical instrument or the patient, is trackable in the imaging mode based on the image data of the primary imaging unit, and in the parking mode based on the image data of the secondary imaging unit.

As the primary imaging unit can be moved into the parking mode remote from the surgical field, a hindrance of the therapy execution by the primary imaging unit is avoided, while the medical instrument or the patient is still trackable.

In particular, the primary imaging unit being arranged to determine the position of the secondary imaging unit enables a seamless transition of object tracking from the primary to the secondary imaging unit when the primary imaging unit needs to be moved away from the surgical mode, i.e. needs to be moved into the parking mode. Thus, a particular efficient object tracking may be achieved, without the need for any additional global tracking means.

The term "imaging mode" relates to a position in which the primary imaging unit is arranged in a suitable position close to the object to provide first image data of the object.

The term "parking mode" relates to a position in which the primary imaging unit is more remote from a patient's body than in the imaging mode. In the parking mode, it is impossible for the primary imaging unit to provide first image data of the object. There is e.g. no free line of sight to the surgical area or the distance or the angle is unsuitable to provide first image data of the object.

The term "reference point" relates to a point in the operating room, which position relative to the position of the primary imaging unit is known and can therefore be used to calculate the position of the secondary imaging unit relative to the position of the primary imaging unit. The reference point is preferably the position of the primary imaging unit.

The term "predetermined movable object" relates to a medical instrument and/or a patient.

In an example, the primary imaging unit comprises a 2D and/or 3D X-ray image acquisition system. The secondary imaging unit may comprise at least one camera capable of detecting body or instrument properties visible from the outside, for example a visible light or infrared camera. The primary imaging unit may, in addition to an X-ray imaging unit, comprise an additional imaging unit including at least one further optical camera, which is likewise arranged to capture the surgical field on the patient table. For both imaging units, the optical cameras can be fixedly positioned to each other. Both imaging units can submit continuous/current/life image data. Both imaging units can be capable of a 3D reconstruction of e.g. the body.

In a further example, the primary imaging unit is connected to a basis with a C-shaped arm and the secondary imaging unit is connected to a fixture. The secondary imaging unit and/or the fixture are preferably at least temporally fixedly attachable to an object support, which might be a patient table, or to the ceiling, the floor or elsewhere in the operating room.

In a preferred embodiment, the secondary imaging unit comprises a surgical task light, that is, a surgical task light as known per se in the art is preferably provided with at least one camera for providing the second image data.

The secondary imaging unit might also be movable and therefore a movement sensor might be provided to detect movements of the secondary imaging unit. If a movement of the secondary imaging unit is detected, a user can be informed.

In an example, current image data of the primary and the secondary imaging unit are merged in the imaging mode. The result is preferably an X-ray image overlaid with an optical image to track the patient or medical instrument. Therefore, the preferred object tracking device for a medical imaging system offers not only a real time patient and/or instrument motion display of the patient exterior via video guidance and a real time patient and/or instrument motion display of the patient interior via X-ray, but also a merging of both.

In a further example, in the parking mode, only the secondary imaging unit provides current second image data of the exterior of a patient's body. However, these second image data can preferably be merged with previously captured and stored image data of the primary imaging unit. If a necessity for imaging guidance/update/check up of the first image data occurs, the primary imaging unit is positioned back from the parking mode into the imaging mode and new first image data of the interior of the body are acquired. The merge of the first and second imaging data is then automatically updated with the new information.

For the preferred merging of the first image data from e.g. the X-ray system and the second image data from e.g. the video camera, the position of the secondary imaging unit relative to the primary imaging unit needs to be known and therefore to be determined and monitored.

Consequently, preferably the position of the secondary imaging unit is monitored relative to the position of the primary imaging unit. The position monitoring can be done by means of a position sensor monitoring the position of the secondary imaging unit or can be derived from the image data generated by the primary imaging unit and the secondary imaging unit itself. Such position monitoring may be based on detection of a characteristic or fiducial in both images, as explained later, or it may comprise another optical or non-optical position monitoring system like an optical shape sensing system, an electromagnetic tracking system, articulated arms, a radio frequency tracking system et cetera.

In an example, if the positions of the primary and the secondary imaging units are known to each other, image data acquired by one imaging unit can then be registered and merged to the image data acquired by the other imaging unit. The object tracking can be controlled by one imaging unit, while the other one imaging unit need not be calibrated in position manually. Hence, no calibration is required.

Preferably, the position of the secondary imaging unit is monitored relative to the position of the primary imaging unit. The image data acquired by the secondary imaging unit can then be registered and merged to the image data acquired by the first imaging unit without a time consuming and complex calibration of the secondary imaging unit.

According to an example, the primary and secondary imaging units are configured to determine a position of a determined characteristic or a fiducial on the object. The positions of the characteristic or fiducial in the first and second image data can then be determined in relation to each other, from which a position of the secondary imaging unit with respect to the primary imaging unit can be derived. In a preferred embodiment, for this purpose, the first optical image data provided by the camera of the additional imaging unit is combined with the second optical image data provided by the camera of the secondary imaging unit.

A characteristic can be e.g. a determined end of an instrument or a determined physical feature of the patient. A fiducial can be a passive marker, which does not actively send optical radiation to the imaging units, or it can be an active marker, i.e. a light source sending radiation to the imaging units. For instance, the fiducial can be an infrared light source and the cameras in the secondary and additional imaging units can be infrared sensitive cameras for acquiring infrared images showing the infrared light fiducial.

The fiducial is preferably arranged on the patient or on the instrument. Preferably several fiducials are used to determine the position of the secondary imaging unit e.g. relative to the primary imaging unit. Thereto, preferably, cameras in both imaging units are aimed at the fiducial. The thereby acquired first optical image data show the position of the fiducial relative to the primary imaging unit and the acquired second optical image data show the position of the fiducial relative to the secondary imaging unit. By overlapping the relative positions of the fiducial in the primary and secondary image data, the relative positions and orientations of the primary imaging unit and the secondary imaging unit are calculated. In particular, the position of the secondary imaging unit relative to the position of the primary imaging unit is calculated. The same applies, if a characteristic or a combination of characteristic and fiducial is used instead of the fiducial. With this knowledge, the image data from both imaging units, in particular X-ray image data from the primary imaging unit and optical image data from the secondary imaging unit, can be merged.

With every update of the primary and secondary imaging data, the relative positions of the primary and secondary imaging unit are updated. In some embodiments described below, a primary imaging unit may be provided with a position sensor and/or a movement sensor to monitor position(s) of the secondary imaging unit and/or to detect movement(s) of the secondary imaging unit so as to update the relative positions of the primary and secondary imaging units. In some embodiments described below, a fiducial may be used to update relative positions of the primary and secondary imaging units. When one (or both) imaging units are moved, the relative positions of the primary and secondary imaging units are recalculated relative to the fiducial and relative to each other as long as both imaging units maintain a line of sight on the fiducial. If the line of sight of the primary imaging unit on the fiducial is lost, the tracking of the patient and/or the instrument is taken over by the secondary imaging unit.

In a further example, the secondary imaging unit and/or the additional imaging unit comprises a hyperspectral camera capable of monitoring the exterior of the body in different spectral wavelength bands.

In a further example, the secondary imaging unit and/or the additional imaging unit is capable of tracking a laparoscope and is able to extend the laparoscopic view with X-ray view data obtained from one of the imaging units.

According to a further example, the primary imaging unit tracks at least a first object (e.g. a medical instrument) and the secondary imaging unit tracks at least a second object (e.g. a patient or part of her/him).

According to the present invention, the medical imaging system may further comprise an image acquisition device, an object support e.g. in form of a patient table, a control unit and a display device.

The display device, arranged e.g. at the secondary imaging unit, may comprise a monitor to present the data acquired by the first and/or the secondary imaging unit. The medical imaging system and in particular the secondary imaging unit may further comprise a surgical light to illuminate the surgical area.

According to the present invention, also an object tracking method for a medical imaging system to track a predetermined movable object, as a patient or a medical instrument, is presented. It comprises the following steps:
a) providing image data of a patient's body by a primary imaging unit, which is movable between an imaging mode and a parking mode,
b) providing image data of a patient's body by a secondary imaging unit, and
c) monitoring, by the primary imaging unit, a position of the secondary imaging unit relative to the position of a reference point, and
d) tracking the predetermined movable object:
when the primary imaging unit is in the imaging mode, based on the imaging of the primary imaging unit, and
when the primary imaging unit is in the parking mode, based on the imaging of the secondary imaging unit.

In an example, in the imaging mode, as the position of the secondary imaging unit relative to the primary imaging unit is known, the first image data from the X-ray system and the second image data from the optical camera can be merged. This provides preferably the X-ray imaging overlaid with the optical imaging to track the patient or the medical instrument.

In a further example, in the parking mode, when the primary imaging unit is more remote from the patient's body, only the secondary imaging unit provides current second image data of the patient's body, preferably optical image data. However, these second image data can still be merged with previously captured and stored image data of the primary imaging unit. If a necessity for imaging guidance/update/check up of the first image data occurs, the basis with the C-shaped arm and the primary imaging unit is positioned back from the parking mode into the imaging mode and new first image data of the interior of the body are made. The merging of the first and second imaging data is then automatically updated with the new information.

In a further example of the present invention, an object tracking computer program for tracking a predetermined movable object is presented, wherein the computer program comprises program code means for causing an object tracking device as defined in the independent device claim to carry out the steps of the object tracking method as defined in the independent method claim, when the computer program is run on a computer controlling the object tracking device.

According to an aspect of the present invention, the primary imaging unit the X-ray unit is supplemented by the secondary imaging unit. The tracking purpose is provided by the secondary unit. Since the secondary unit can be provided somewhat smaller, more available and thus free workspace is provided. Advantageously, the secondary imaging unit is integrated with a surgical task light as commonly used during interventional or surgical procedures, so that no additional devices need be provided.

Further, preferably, the primary imaging unit is provided with an additional imaging unit comprising at least one camera; the additional imaging unit is, for example, integrated in a housing of a detector of the X-ray unit, so that an automatic registration of the X-ray images and the optical images provided by the additional imaging unit is obtained.

In other words, a slave tracking system is embedded into the slave or secondary imaging unit, being attached to the operating table and coupled to the video camera set located in the additional imaging unit of the master or primary imaging unit. A continuous real-time communication between a master set of four video cameras in the additional imaging unit, and a slave set of two cameras in the secondary imaging unit makes sure that a spatial location of the slave imaging unit is established and determined spatial wise.

Once the C-arm of the master imaging system is considered to hinder the therapy execution, the slave imaging unit seamlessly takes over the guidance, thus allowing the C-arm to be temporarily parked away from the surgical field. Once the need arises to provide for either 2D or 3D X-ray imaging, the C-arm can be moved back to the imaging or working position and the object tracking may be transferred back from the slave imaging unit to the master imaging unit.

The invention provides both for the patient and instrument tracking in the minimally invasive therapy settings, with a continuous availability for the imaging guidance/update/check up with the C-arm located in a close proximity.

It shall be understood that the medical imaging system, the object tracking method for a medical imaging system, the computer program element for controlling such device and the computer readable medium having stored such computer program element according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

Figure 1:
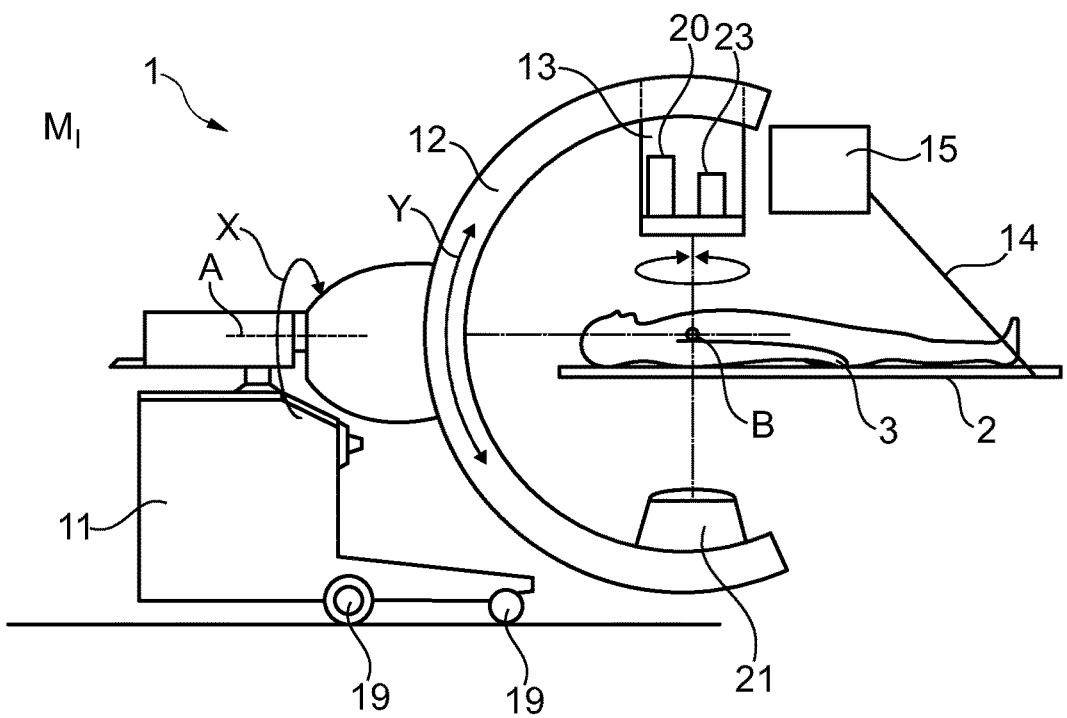
FIG. 1 shows a schematic drawing of an example of a medical imaging system with two imaging units, where both imaging units are present above, around and below the patient.

FIG. 1 shows schematically and exemplarily an embodiment of a medical imaging system according to the invention. The medical imaging system comprises an object tracking device 1, an object support in form of e.g. a patient table 2, a control unit (not shown) and a display device (not shown). The object tracking device 1 according to the invention serves for tracking a predetermined movable object, as a patient 3 or a medical instrument. It comprises a basis 11 with a C-shaped arm 12 and a primary imaging unit 13 and a fixture 14 with a secondary imaging unit 15.

The basis 11 is movable relative to the patient table 2 and is thereto mounted on wheels 19. It is not necessary that the basis 11 is attached to the patient table 2. The C-shaped arm 12 encloses in the shown position in FIG. 1 the patient table 2. In other words, it is arranged above, around and below the patient table 2. The C-shaped arm 12 is rotatable relative to the basis 11 and relative to the patient 3. An angular rotation of the C-shaped arm 12 around a first axis A in the direction of arrow X and/or an orbital rotation around a second axis B in the direction of arrow Y are possible.

The primary imaging unit 13 is arranged in the object tracking device 1, and in particular in the C-shaped arm 12. It is configured to provide first image data, as explained further below, e.g. of the interior of a patient's body. Therefore, the primary imaging unit 13 comprises a 2D and/or 3D X-ray system in form of an X-ray detector 20 in the upper branch of the C-shaped arm 12 and an X-ray source 21 in the lower branch of the C-shaped arm 12. The 2D and/or 3D X-ray system can comprise one or more X-ray cameras. The X-ray source 21 and the X-ray detector 20 are controlled by the control unit (not shown). The X-rays generated in the X-ray source 21 traverse the patient 3 and the patient table 2, and the traversed X-rays are then detected by the X-ray detector 20. The X-ray detector 20 and the X-ray source 21 are positioned at the ends of the C-shaped arms 12. They are generally arranged to capture the surgical field on the patient table 2. The C-shaped arm 12 is rotatable relative to the basis 11 and relative to the patient 3 to allow the primary imaging unit 13 to provide an actual image showing a desired region within the patient 3 in a desired direction.

The first image data are a three-dimensional image data set being, in this embodiment, a three-dimensional computed tomography image data set. In other embodiments, the image data set can also be a two-dimensional image data set. Moreover, the image data set can be the image data set of another imaging modality like a magnetic resonance, ultrasound, single photon emission computed tomography, and positron emission tomography.

An additional imaging unit 23, as a camera sensitive to ultraviolet light (UV light), Infrared light (IR light) and/or light with visible wavelengths is further attached to the upper branch of the C-shaped arm 12, here aside to the X-ray detector 20. This camera is also arranged to capture the surgical field on the patient table 2. Preferably, a set of, for example, four cameras is arranged along different side of the X-ray detector and integrated in the housing thereof.

It must be noted that the C-arm is shown as an example. Of course, also other movable X-ray imaging units can be provided, as for example an X-ray system attached to e.g. a rail on the ceiling, a wall or the floor, or an X-ray system attached to a robotic arm.

The fixture 14 with the secondary imaging unit 15 is attached to the patient table 2 and is enabled to capture the surgical field on the patient table 2. The secondary imaging unit 15 can also be arranged elsewhere in the operating room. Preferably, the secondary imaging unit 15 further comprises a surgical task light.

The fixture 14 and/or the secondary imaging unit 15 can be movable relative to the patient table 2. The secondary imaging unit 15 is configured to provide second image data e.g. of the exterior of a patient's body, preferably optical image data. It comprises therefore at least one camera capable of detecting discontinuously or continuously the body properties visible from the outside. The secondary imaging unit 15 is also capable of tracking instruments. Preferably, the secondary imaging unit 15 comprises a set of, for example, two cameras.

However, the secondary imaging unit 15 might also be exclusively or additionally configured to provide image data of the interior of a patient's body.

The control unit (not shown) merges discontinuously or continuously the first and the second image data and displays them on a monitor (not shown). It provides therefore an X-ray imaging overlaid with the video imaging to track the predetermined movable object, as a patient 3 or a medical instrument. As a result, the exemplary object tracking device 1 for a medical imaging system offers not only a real time patient and/or instrument motion display of the patient exterior via video guidance and a real time patient and/or instrument motion display of the patient interior via X-ray, but also a merge of both.

The term "merge" relates to an integration of the first and second image data into one view.

To merge the first image data from the X-ray system and the second image data from the video camera, the position of the secondary imaging unit 15 relative to the primary imaging unit 13 needs to be known and therefore to be monitored. In the shown embodiment, the position of the secondary imaging unit 15 is monitored relative to the position of the primary imaging unit 13. In another embodiment, the position of the secondary imaging unit 15 can be monitored relative to a reference point, for example a predetermined fixed point in the operating room, which position relative to the position of the primary imaging unit 13 is known and can be used to calculate the position of the secondary imaging unit 15 relative to the position of the primary imaging unit 13.

In other words, if position and orientation of the local coordinate systems of the primary and the secondary imaging units are known relative to each other, image data acquired by one imaging unit can be merged with the image data acquired by the other imaging unit. An object tracking method according to the invention can be controlled by one imaging unit, while the other one imaging unit need not be calibrated in position manually. Hence, no calibration is required.

Figure 2:
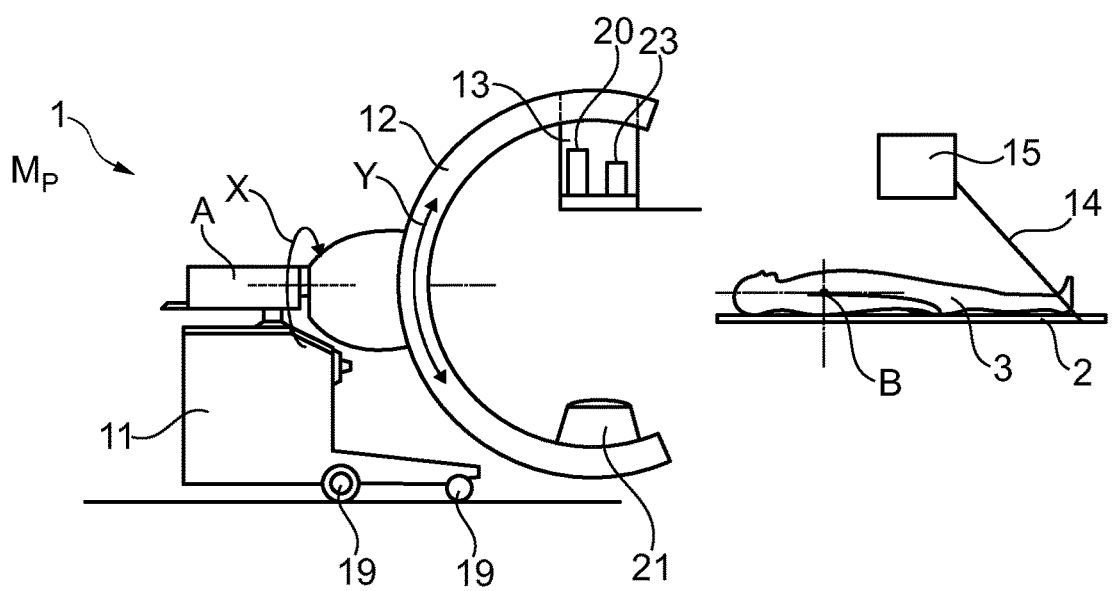
FIG. 2 shows a schematic drawing of an example of the medical imaging system, where only one, i.e. the secondary imaging unit is present above the patient, while the other, i.e. the primary imaging unit is parked aside.

To provide the object tracking device 1 for a medical imaging system and a medical imaging system, which do not hinder during the therapy execution, the basis 11 with the C-shaped arm 12 is movable between an imaging mode $M_I$ shown in FIG. 1 close to the patient table 2 and a parking mode $M_P$ shown in FIG. 2 more remote from the patient table 2.

FIG. 2 shows therefore a schematic drawing of the medical imaging system in a situation, where only the secondary imaging unit 15 is present above the patient 3, while the basis 11 with the C-shaped arm 12 and the primary imaging unit 13 is parked aside. In this parking mode, the basis 11 with the C-shaped arm 12 does not hinder a physician and/or medical staff during the therapy execution. In the parking mode, only the secondary imaging unit 15 provides current second image data of the exterior of a patient's body. However, these second image data can still be merged with previously captured and stored image data of the primary imaging unit 13. If the need for imaging guidance/update/check up of the first image data arises, the basis 11 with the C-shaped arm 12 and the primary imaging unit 13 is positioned back from the parking mode into the imaging mode and new first image data of the interior of the body are made. The merging of the first and second imaging data is then automatically updated with the new image information of the primary imaging unit 13

An exemplary object tracking method for a medical imaging system to track a predetermined movable object, such as a patient 3 or a medical instrument, therefore comprises the following steps as indicated by FIGS. 1 and 2:

a) Providing image data of the patient's body and/or the medical instrument by the primary imaging unit 13 being in the imaging mode close to a patient's body as shown in FIG. 1. The primary imaging unit 13 is an X-ray system configured to provide X-ray image data of the interior of a patient's body. The primary imaging unit 13 is movable between the imaging mode $M_I$ (FIG. 1) and a parking mode $M_P$ (FIG. 2) more remote from a patient's body.

b) Providing image data of the patient's body and/or the medical instrument by the secondary imaging unit 15. The secondary imaging unit 15 is a photo and/or video camera capable of detecting body properties visible from the outside.

c) Monitoring a position of the secondary imaging unit 15 relative to the position of a reference point, which can be the position of the primary imaging unit 13. The monitoring is done by the position monitoring arrangement, which can be provided by a sensor or the primary and secondary imaging units itself by means of fiducials 30, as described in detail below to FIG. 3. In embodiment, the primary imaging unit 13 comprises a position sensor 24 to monitor the position of the secondary imaging unit 15.

d) Tracking the patient's body and/or the medical instrument in the imaging mode $M_I$ (FIG. 1) based on the imaging of the primary imaging unit 13, and in the parking mode $M_P$ (FIG. 2) based on the imaging of the secondary imaging unit 15.

In the imaging mode $M_I$ (FIG. 1), as the position of the secondary imaging unit 15 relative to the primary imaging unit 13 is known, the first image data from the X-ray system and the second image data from the photo and/or video camera can be merged. This provides the X-ray imaging overlaid with the photo and/or video imaging to track the patient 3 or the medical instrument.

In the parking mode $M_P$ (FIG. 2), when the primary imaging unit 13 is more remote from the patient's body, only the secondary imaging unit 15 provides current second image data of the patient's body. However, these second image data can still be merged with previously captured and stored image data of the primary imaging unit 13. If a necessity for imaging guidance/update/check up of the first image data occurs, the basis 11 with the C-shaped arm 12 and the primary imaging unit 13 is positioned back from the parking mode (FIG. 2) into the imaging mode (FIG. 1) and new first image data of the interior of the body are made. The merge of the first and second imaging data is then automatically updated with the new information.

Figure 3:
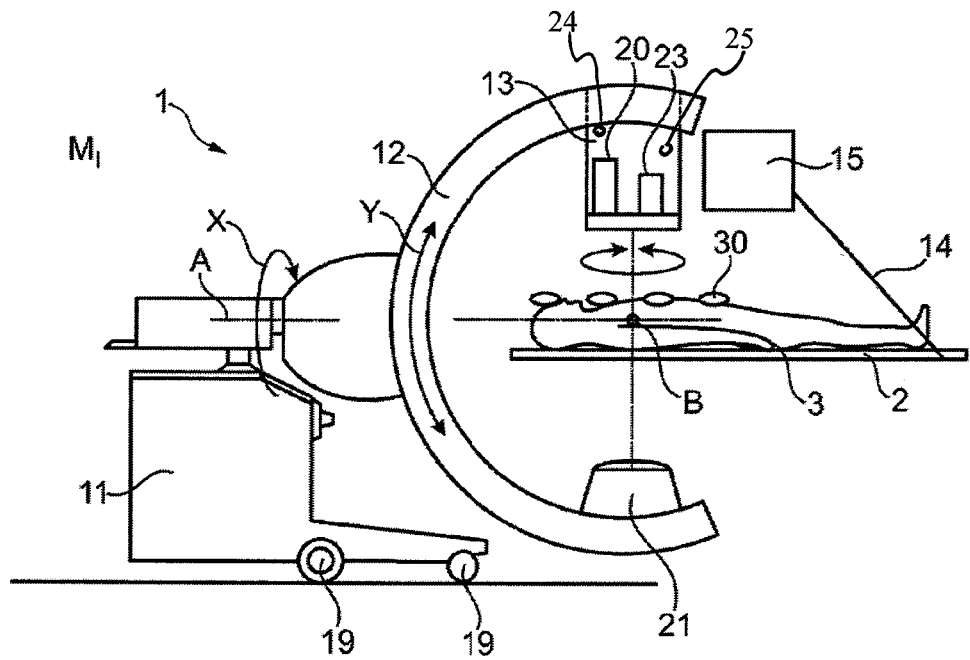
FIG. 3 shows a schematic drawing of an example of a medical imaging system in a situation similar to FIG. 1, where fiducials are used to determine the position of the secondary imaging unit relative to the primary imaging unit.

FIG. 3 shows a schematic drawing of a medical imaging system in a situation similar to FIG. 1, where fiducials 30 are used to determine the position of the secondary imaging unit 15 relative to the primary imaging unit 13. The fiducials 30 can be passive markers, which do not actively send optical radiation to the imaging units, or they can be active markers, i.e. light sources sending radiation to the imaging units. For instance, the fiducials 30 can be infrared light sources and the imaging units can be infrared sensitive for acquiring infrared images showing infrared light fiducials 30.

As shown in FIG. 3, preferably four fiducials 30 are used to form a fiducial model to determine a reliable position of the secondary imaging unit 15. The fiducials 30 are arranged on the patient. Both imaging units 13, 15 are aimed at the fiducials 30. The thereby acquired primary image data show the position of the fiducials 30 relative to the primary imaging unit 13 and the acquired secondary image data show the position of the fiducials 30 relative to the secondary imaging unit 15. By registering the positions of the fiducials 30 in the primary and secondary image data relative to each other, the position of the secondary imaging unit 15 relative to the position of the primary imaging unit 13 is calculated.

With this knowledge, the image data from both imaging units 13, 15 can be merged, and a seamless transition of object tracking from the primary imaging unit 13 to the secondary imaging unit 15 may be provided if the primary imaging unit 13 needs to be moved away from the surgical field.

With every update of the primary and secondary imaging data, the relative positions of the primary and secondary imaging units 13, 15 may be updated. When one (or both) imaging units are moved, the relative position of the primary and secondary imaging unit 13 is recalculated as long as both imaging units maintain a line of sight on the fiducials 30.

If the line of sight of the primary imaging unit 13 is lost, for example because the primary imaging unit is moved into parking mode, the tracking of the patient 3 and/or the instrument is taken over by the secondary imaging unit 15. Vice versa, if the line of sight of the secondary imaging unit 15 were lost, the tracking of the patient 3 and/or the instrument would be taken over by the primary imaging unit 13. The same can be achieved, if particular characteristics of the object are used instead of the fiducials 30.

In other words, the slave camera system of the slave or secondary imaging unit may comprise two or more cameras rigidly connected to each other. The relation between the cameras and the intrinsic parameters of the cameras are calibrated on a similar way as the master camera system attached to the detector. The slave camera system is attached to the ceiling, floor or to the patient table, or is integrated with a surgical task light, and is aimed on the fiducials 30 on the patient or the instruments. With the calibrated slave camera system, the pose of the slave camera system relative to a fiducial model can be calculated. The fiducial model is created by the detector camera system from the attached fiducials on the patient or instrument. If the pose of the slave camera system is known relative to a fiducial model, it is also possible to calculate the pose of the slave camera system relative to the X-ray system.

If the slave camera system is moved the pose of the slave camera system can be updated as long as both camera systems have line of sight on a fiducial model. If the slave camera system is correctly positioned the detector camera system can be moved until it loses line of sight on a fiducial model. If the line of sight with the detector camera system is lost the tracking of the patient and/or instrument is taken over by the slave camera system. It could also be a combination that one instrument is tracked with the detector camera system and the patient is for example tracked with the slave camera system.

If the slave camera system is tracking, the slave camera should not be moved when the detector camera system has no line of sight. Therefore we propose to add a movement sensor to the slave camera system to detect movements. If a movement of the slave camera system is detected the user can be informed. In one embodiment, the primary imaging unit 13 is provided with a movement sensor 25 to detect movements of the secondary imaging unit 15.

The fiducial model must consist out of at least four fiducials to be able to determine reliable the pose of the slave camera system.

As a result, thereby a continuous real-time communication between preferably four video cameras in the X-ray detector 20 of the primary imaging unit 13 and preferably two video cameras in the secondary imaging unit 15 is enabled.

Both, the primary and the secondary imaging units 15 can operate directly and can be controlled from only one of the two imaging units. The controlling imaging unit is preferably the primary imaging unit 13. However, also a performing of interventions on the patient's body guided by the secondary imaging unit 15 is possible.

It is also possible that the primary imaging unit 13 tracks a first object (e.g. a medical instrument) and the secondary imaging unit 15 tracks a second object (e.g. a patient 3 or part of her/him).

The embodiments of the invention can be used during minimally invasive procedures requiring object tracking by X-ray such as needle biopsies, radio frequency ablations, et cetera. The invention is foreseen to be used e.g. in the following clinical settings: minimally invasive trauma surgery, minimally invasive orthopaedic surgery, minimally invasive neuro-surgical therapy, minimally invasive laparoscopic therapy, minimally invasive endoscopic therapy, minimally invasive gynaecology, minimally invasive urology, minimally invasive bronchoscopic procedures.

The imaging system will be continuously present above the surgical/interventional field for the purposes of the image-guided-therapy. The patient and instrument tracking can be continuated when needs arise to temporarily remove primary imaging unit to its parking position. Further, a repeated possibility to take the patient and instrument navigation from the primary imaging unit and back is enabled in accordance with the present clinical circumstances and without any interruption of the therapy.

Figure 4:
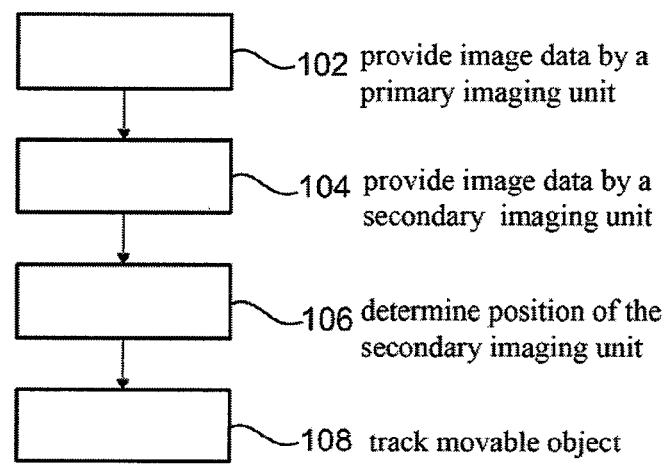
FIG. 4 shows basic steps of an example of a method for a medical imaging system to track a predetermined movable object.

FIG. 4 shows a schematic overview of steps of an object tracking method 100 for a medical imaging system to track a predetermined movable object. The method, as indicated above, comprises the following steps, not necessarily in this order:

In a first step 102, image data of a patient's body is provided by a primary imaging unit, which is movable between an imaging mode and a parking mode.

In a second step 104, image data of a patient's body is provided by a secondary imaging unit.

In a third step 106, a position of the secondary imaging unit relative to the position of a reference point is determined by means of the primary imaging unit.

In a fourth step 108, the predetermined movable object is tracked i) in the imaging mode based on the imaging of the primary imaging unit (13), and ii) in the parking mode based on the imaging of the secondary imaging unit (15).

The first step 102 is also referred to as step a), the second step 104 as step b), the third step 106 as step c), and the fourth step 108 as step d).

In other words, the object tracking method 100 for a medical imaging system is a method where the primary or master imaging unit of the medical system takes a 3D image of the interior of the body, the master imaging unit determines the position of the secondary or slave imaging unit, the camera of the slave imaging unit makes an image of the exterior of the body, the medical system registers the interior and the exterior image to each other using the position of the slave imaging unit relative to the master imaging unit, the master imaging unit is positioned away from the body, interventions on the body are performed guided by the slave imaging unit.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it, which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A medical imaging system arranged for tracking a predetermined movable object, comprising:
    a primary imager configured to provide first image data of a patient's body, the primary imager being movable between a first position at an imaging mode and a second position at a parking mode, the second position being remote from the first position where the primary imager is unable to provide the first image data from the second position, wherein the primary imager is configured to provide image data of an interior of a patient's body as the first image data;
    a secondary imager configured to provide second image data of the patient's body, and to provide image data of an exterior of the patient's body as the second image data, the second image data being current image data, wherein the second image data are merged with previously captured and stored first image data; and
    a controller configured to: cause the primary imager to track the predetermined movable object based on the first image data when the primary imager is in the imaging mode; cause the secondary imager to track the predetermined movable object based on the second image data when the primary imager is in the parking mode; determine a position of the secondary imager relative to a reference position; and continuously present a live view of a surgical/interventional field based on first image data that is obtained live when the primary imager is in the first position and based on second image data that is obtained live when the primary imager is in the first position, and based on the previously captured and stored first image data when the primary imager is temporarily moved to the second position and based on second image data that is obtained live when the primary imager is temporarily moved to the second position.

2. The medical imaging system according to claim wherein the primary imager comprises:
    an X-ray imager, and
    an additional imager comprising at least one camera for providing first optical image data of the patient's body.

3. The medical imaging system according to claim 2, wherein the secondary imager comprises at least one camera to provide second optical image data as the second image data.

4. The medical imaging system according to claim 3, wherein the predetermined movable object includes a fiducial, wherein the additional imager and the secondary imager are configured to detect a position of a determined characteristic or the fiducial on the predetermined movable object, and wherein the controller is configured to derive the position of the secondary imager from relative positions of the determined characteristic or fiducial in the first and second optical image data.

5. The medical imaging system according to claim wherein the primary imager comprises a position sensor configured to monitor the position of the secondary imager.

6. The medical imaging system according to claim 1, wherein the reference position is a position of the primary imager.

7. The medical imaging system according to claim 6, wherein, when the primary imager is in the imaging mode where the primary imager provides the first image data and the secondary imager provides second image data, the controller is configured to merge current image data of the primary imager and current image data of the secondary imager.

8. The medical imaging system according to claim 7, wherein, when the primary imager is in the parking mode, the controller is configured to merge previously captured image data of the primary imager and current image data of the secondary imager.

9. The medical imaging system according to claim 1, wherein the primary imager is configured to track at least a first object and the secondary imager is configured to track at least a second object.

10. The medical imaging system according to claim 9, wherein the second imager further comprises a surgical task light.

11. The medical imaging system according to claim 10, further comprising an object support configured to support the secondary imager, wherein the secondary imager is at least temporally fixedly attachable to the object support.

12. The medical imaging system according to claim 11, wherein the primary imager is provided with a movement sensor to detect movements of the secondary imager.

13. An object tracking method for a medical imaging system to track a predetermined movable object, the method comprising:
    providing first image data of a patient's body by a primary imager, which is movable between a first position at an imaging mode and a second position at a parking mode, the second position being remote from the first position where the primary imager is unable to provide the first image data from the second position, wherein the first image data provided by the primary imager is image data of an interior of a patient's body;
    providing second image data of the patient's body by a secondary imager, wherein the image data provided by the secondary imager are current data, and are image data of an exterior of the patient's body;

determining, by a controller, a position of the secondary imager relative to a reference position;

merging the second image data with previously captured and stored first image data;

tracking the predetermined movable object: in the imaging mode based on the first image data from the primary imager, and in the parking mode based on the second image data from the position of the secondary imager; and continuously presenting a live view of a surgical/interventional field based on first image data that is obtained live when the primary imager is in the first position and based on second image data that is obtained live when the primary imager is in the first position, and based on the previously captured and stored first image data when the primary imager is temporarily moved to the second position and based on second image data that is obtained live when the primary imager is temporarily moved to the second position.

14. A non-transitory computer readable medium comprising computer instructions which, when executed by a processor, configure the processor to implement a process that includes:

causing a primary imager to provide first image data of a patient's body, the primary imager being movable between a first position at an imaging mode and a second position at a parking mode, the second position being remote from the first position where the primary imager is unable to provide the first image data from the second position, wherein the first image data provided by the primary imager is image data of an interior of a patient's body;

providing a secondary imager to provide second image data of the patient's body, wherein the image data provided by the secondary imager is image data of an exterior of the patient's body;

determining a position of the secondary imager relative to a reference position;

merging the second image data with previously captured and stored first image data; and tracking a predetermined movable object:

in the imaging mode based on the first image data from the primary imager, and in the parking mode based on the second image data from the position of the secondary imager; and continuously presenting a live view of a surgical/interventional field based on first image data that is obtained live when the primary imager is in the first position and based on second image data that is obtained live when the primary imager is in the first position, and based on the previously captured and stored first image data when the primary imager is temporarily moved to the second position and based on second image data that is obtained live when the primary imager is temporarily moved to the second position.

15. The non-transitory computer readable medium of claim 14, wherein the primary imager provides the first image data and the secondary imager provides second image data in the imaging mode, and wherein the primary imager is located remote from the predetermined movable object and unable to provide the first image data in the parking mode.

16. The non-transitory computer readable medium of claim 14,
wherein the predetermined movable object is tracked and continuously presented in the live view of the surgical/interventional field when the primary imager returns to the first position from the second position.

17. The non-transitory computer readable medium of claim 16,
wherein the live view when the primary imager returns to the first position is again based on first image data that is obtained live when the primary imager is in the first position and based on second image data that is obtained live when the primary imager is in the first position.

18. The non-transitory computer readable medium of claim 14,
wherein merging of the first image data and the second image data is based on a known relative positioning between the primary imager and the secondary imager.

19. The non-transitory computer readable medium of claim 18,
wherein the merging is independent of calibration between the secondary imager and the primary imager.

* * * * *